United States Patent [19]

Blank et al.

[11] 4,370,499

[45] Jan. 25, 1983

[54] 3-NITRO-ACETOACETANILIDES, PROCESSES FOR THEIR PREPARATION AND THEIR USE

[75] Inventors: Heinz U. Blank, Odenthal; Erich Wolters, Niederzier; Karl W. Müller, Leverkusen; Günter Rottloff, Cologne, all of Fed. Rep. of Germany

[73] Assignee: Bayer Aktiengesellschaft, Leverkusen, Fed. Rep. of Germany

[21] Appl. No.: 263,388

[22] Filed: May 13, 1981

[30] Foreign Application Priority Data

May 29, 1980 [DE] Fed. Rep. of Germany ....... 3020443

[51] Int. Cl.$^3$ .......................................... C07C 103/34
[52] U.S. Cl. .................................................. 564/200
[58] Field of Search ...................................... 564/200

[56] References Cited

U.S. PATENT DOCUMENTS

| | | | |
|---|---|---|---|
| 2,152,786 | 4/1939 | Boese, Jr. | 564/200 X |
| 2,311,054 | 2/1943 | Kenyon et al. | 564/200 |
| 2,714,117 | 7/1955 | Lacey et al. | 564/200 X |
| 2,734,051 | 2/1956 | Iselin | 564/200 X |
| 3,347,908 | 10/1967 | Pfister et al. | 564/200 X |
| 3,361,736 | 1/1968 | Ribka | 564/200 X |
| 3,567,765 | 3/1971 | Thiele | 564/200 X |
| 3,907,494 | 9/1975 | Saygin | 564/200 X |
| 4,014,679 | 3/1977 | Perronnet et al. | 564/200 X |

FOREIGN PATENT DOCUMENTS

| | | | |
|---|---|---|---|
| 988553 | 8/1951 | France | 564/200 |
| 51-7500 | 7/1976 | Japan | 564/200 |
| 602104 | 5/1948 | United Kingdom | 564/200 |

OTHER PUBLICATIONS

Schwarz et al., CA52:20055c (1953).

*Primary Examiner*—Thomas A. Waltz
*Attorney, Agent, or Firm*—Sprung, Horn, Kramer & Woods

[57] ABSTRACT

3-Nitro-acetoacetanilides of the formula

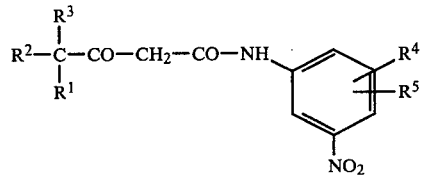

in which
$R^1$, $R^2$ and $R^3$ independently of one another represent hydrogen, alkyl, cycloalkyl or aryl, it being possible for two of the said radicals to form a cycloaliphatic ring together with the carbon atom on which they are substituents, and
$R^4$ and $R^5$ independently of one another denote hydrogen, alkyl, aralkyl, aryl, alkoxy, alkylthio, aralkoxy, aralkylthio, aryloxy, arylthio, halogen, nitro or amino disubstituted by alkyl, aralkyl or aryl, and
$R^4$ and $R^5$, when they are adjacent, can be parts of a fused cycloaliphatic or aromatic ring, are described as well as methods for its preparation such as by reaction of an acetoacetic acid compound with a 3-nitro-aniline under condensation conditions, or, by reaction of an enamine with 3-nitro-phenyl isocyanate. The 3-nitro-acetoacetanilides are useful intermediates in the preparation of coupling components for color photography.

1 Claim, No Drawings

3-NITRO-ACETOACETANILIDES, PROCESSES FOR THEIR PREPARATION AND THEIR USE

The present invention relates to 3-nitro-acetoacetanilides, two processes for their preparation and their use for the synthesis of coupling components for colour film photography.

The 3-nitro-acetoacetanilides of the formula (I)

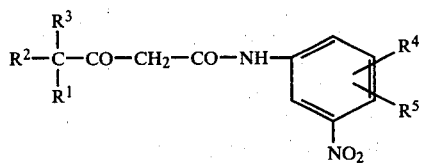

in which
R$^1$, R$^2$ and R$^3$ independently of one another represent hydrogen, alkyl, cycloalkyl or aryl, it also being possible for two of the said radicals to form a cycloaliphatic ring together with the C atom on which they are substituents, and
R$^4$ and R$^5$ independently of one another represent hydrogen, alkyl, aralkyl, aryl, alkoxy, alkylthio, aralkoxy, aralkylthio, aryloxy, arylthio, halogen, nitro or amino disubstituted by alkyl, aralkyl or aryl, and
R$^4$ and R$^5$, when they are adjacent, can be parts of a fused cycloaliphatic or aromatic ring,
have now been found.

Examples of alkyl which may be mentioned are methyl, ethyl, propyl or butyl, preferably methyl or ethyl and particularly preferably methyl.

Examples of cycloalkyl which may be mentioned are cyclopropyl, cyclobutyl, cyclopentyl, cyclohexyl or cycloheptyl and preferably cyclopentyl or cyclohexyl.

Examples of aryl which may be mentioned are phenyl, diphenyl, naphthyl or anthryl and preferably phenyl.

Examples of aralkyl which may be mentioned are benzyl, phenyl-ethyl, naphthyl-methyl, naphthyl-ethyl, anthryl-methyl or anthryl-ethyl and preferably benzyl.

Examples of alkoxy which may be mentioned are methoxy, ethoxy, propoxy or butoxy, preferably methoxy and ethoxy and particularly preferably methoxy.

Examples of alkylthio which may be mentioned are methylthio, ethylthio, propylthio or butylthio and preferably methylthio.

Examples of aralkoxy which may be mentioned are benzyloxy, phenyl-ethoxy, naphthyl-methoxy or anthryl-methoxy and preferably benzyloxy.

Examples of aralkylthio which may be mentioned are benzylthio, phenyl-ethylthio, naphthyl-methylthio or anthryl-methylthio and preferably benzylthio.

Examples of aryloxy which may be mentioned are phenoxy, naphthyloxy or anthryloxy and preferably phenoxy.

Examples of arylthio which may be mentioned are phenylthio, naphthylthio or anthrylthio and preferably phenylthio.

Examples of halogen which may be mentioned are fluorine, chlorine, bromine or iodine, preferably chlorine or bromine and particularly preferably chlorine.

Examples which may be mentioned of amino disubstituted by alkyl, aralkyl or aryl are dimethylamino, diethylamino, dipropylamino, dibutylamino, benzyl-methyl-amino, benzyl-ethyl-amino, dibenzylamino, phenyl-methyl-amino, phenyl-ethyl-amino or diphenylamino. The preferred disubstituted amino is dimethylamino, diethylamino or benzyl-methyl-amino.

In the case where R$^4$ and R$^5$ are adjacent, they can be parts of a fused cycloaliphatic or aromatic ring. In such a case, it is possible, for example, with incorporation of the original aromatic nucleus, to form a compound of the naphthalene series, the indane series or the tetrahydronaphthalene series.

Amongst the compounds according to the invention, 3-nitro-pivaloyl-acetanilides of the formula (II)

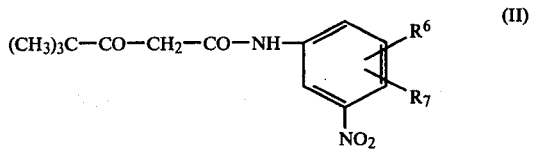

in which
R$^6$ and R$^7$ independently of one another represent hydrogen, methyl, ethyl, methoxy, methylthio, chlorine, bromine, nitro, dimethylamino, diethylamino or benzyl-methyl-amino,
may be mentioned in particular.

Amongst the compounds according to the invention, 2-chloro-5-nitro-pivaloyl-acetanilide of the formula (III)

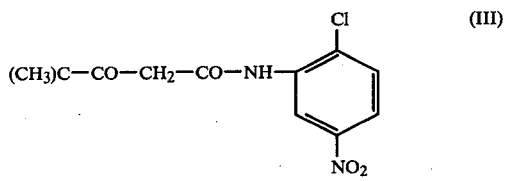

may be mentioned in particular.

Furthermore, a process for the preparation of the 3-nitro-acetoacetanilides of the formula (I)

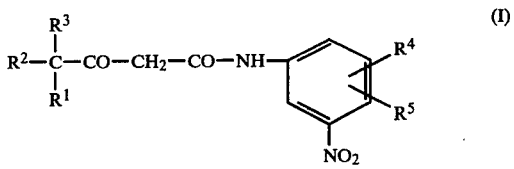

in which
R$^1$, R$^2$ and R$^3$ independently of one another represent hydrogen, alkyl, cycloalkyl or aryl, it being possible for two of the said radicals to form a cycloalkyl ring together with the C atom on which they are substituents, and
R$^4$ and R$^5$ independently of one another denote hydrogen, alkyl, aralkyl, aryl, alkoxy, alkylthio, aralkoxy, aralkylthio, aryloxy, arylthio, halogen, nitro or amino disubstituted by alkyl, aralkyl or aryl, and
R$^4$ and R$^5$, when they are adjacent, can together be parts of a fused cycloaliphatic or aromatic ring,
has now been found, which is characterized in that an acetoacetic acid compound of the formula (IV)

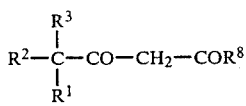 (IV)

in which
R¹, R² and R³ have the meaning indicated and
R⁸ represents alkoxy, chlorine, bromine or the radical

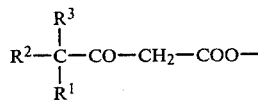

is condensed with a 3-nitroaniline of the formula (V)

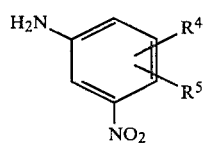 (V)

in which
R⁴ and R⁵ have the meaning indicated above, at a temperature of 50° to 200° C., if appropriate in the presence of an inert diluent.

For examples of the names of the individual radicals, reference may be made to the lists given above.

Examples of the acetoacetic acid compound which may be mentioned are acetoacetic anhydride, an acetoacetyl halide, such as the corresponding chloride or the bromide, or an acetoacetic acid ester, such as the corresponding methyl ester, ethyl ester, propyl ester or butyl ester. In the condensation of acetoacetic anhydride with the 3-nitroaniline, acetoacetic acid is split off, and this can in turn decompose with decarboxylation. In the condensation, according to the invention, with the aid of an acetoacetyl halide, the corresponding hydrogen halide, for example HCl or HBr, is released. This hydrogen halide can be distilled out of the reaction mixture, but it can also be blown out by means of a carrier gas, such as nitrogen, carbon dioxide or argon. However, to remove the free hydrogen halide, it can also be advantageous to bind the latter by adding a suitable base, a salt being formed. Examples of suitable bases for this purpose are tertiary organic amines, such as trimethylamine, triethylamine, dimethylbenzylamine and pyridine. When using an acetoacetic acid ester for the condensation according to the invention, the alcohol corresponding to the ester group, such as methanol, ethanol, propanol or butanol, is split off. This alcohol which has been split off is advantageously removed from the reaction mixture by distillation.

Preferably, one of the said acetoacetic acid esters is used for the condensation according to the invention. The use of the methyl or ethyl ester is particularly preferred. The use of the methyl ester is very particularly preferred.

Amongst the acetoacetic acid esters which are represented by the formula (IV), those which are preferred are again those in which the radicals R¹, R² and R³ denote methyl, so that the condensation is preferably carried out with methyl or ethyl pivaloylacetate of the formula (VI)

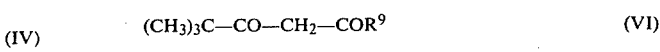 (VI)

in which
R⁹ denotes methoxy or ethoxy.

Acetoacetic acid compounds for the process according to the invention are known to those skilled in the art. Thus, for example, methyl pivaloylacetate can be prepared from methyl pivaloylpyruvate by heating, decarbonylation taking place (U.S. Pat. No. 2,527,306). In the case where the process is to be carried out with the acetoacetyl halides or acetoacetic anhydrides, these can be prepared from the esters by means of reactions known to those skilled in the art.

The 3-nitroanilines of the formula (V) can be used as the 3-nitroanilines for the process according to the invention. Amongst these 3-nitroanilines, those of the formula (VII)

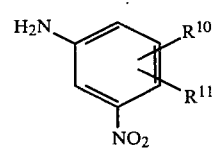 (VII)

in which
R¹⁰ and R¹¹ independently of one another represent hydrogen, methyl, ethyl, methoxy, methylthio, chlorine, bromine, nitro, dimethylamino, diethylamino or methylbenzylamino,
may be mentioned preferentially.

The use of 2-chloro-5-nitro-aniline is very particularly preferred.

Using the condensation of methyl pivaloylacetate and 2-chloro-5-nitro-aniline as an example, the process according to the invention can be illustrated by the following equation:

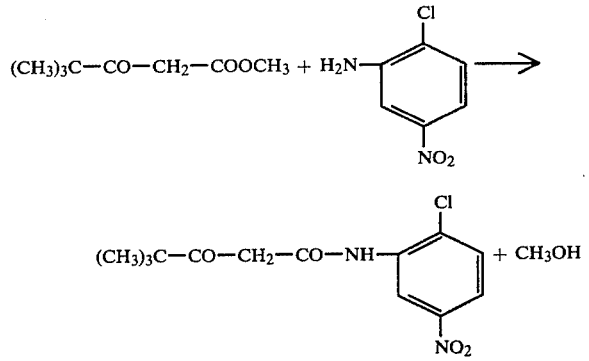

For the reaction, it is necessary for the two reactants to be in a molar ratio of 1:1. However, the reaction of the process according to the invention also proceeds with a different molar ratio until the particular compound which is present in a less than equivalent amount has been consumed. To facilitate the working-up of the reaction mixture, it is advantageous, however, to use the acetoacetic acid compound, preferably the acetoacetic acid ester, in at least a molar amount, relative to the 3-nitroaniline, in order to attain maximum conversion of the nitroaniline, which can only be removed from the end product with difficulty. A molar ratio of acetoacetic acid compound to 3-nitroaniline of 1:1 to 5.1:1 and preferably 1.1:1 to 1.2:1 may be mentioned as an example of at least a molar amount of the acetoacetic acid compound.

The process according to the invention is carried out at a temperature of 50 to 200, preferably 100 to 180 and particularly preferably 120° to 150° C. The process according to the invention is independent of the external pressure and is usually carried out at normal pressure. However, it is known to those skilled in the art to carry out the process using a solvent which boils below the reaction temperature, under a slight excess pressure, or, in order to establish a reflux, to carry out the process with a solvent which boils above the reaction temperature, under a slightly reduced pressure.

The process according to the invention can be carried out with or without a diluent. In the case where a diluent is used, it must be inert towards the reactants. Examples which may be mentioned of inert diluents of this type are aliphatic or aromatic hydrocarbons or their halogen-substituted products, such as 2,2,4-trimethylpentane, benzine fractions with a suitable boiling range, toluene, xylene, chlorobenzene or dichlorobenzene. In the case of the preferred process variant using acetoacetic acid esters, it is preferred to use a diluent which distils off azeotropically with the alcohol which is split off, such as heptane, octane, dichloroethane, trichloroethane, tetrachloroethane, toluene or ethyl butyl ether and preferably toluene. The progress of the condensation reaction can then be followed by the temperature at the head of a distillation column placed on the reaction vessel. This temperature at the head of the column indicates in this case, until the condensation has ended, the boiling point of the azeotrope consisting of the alcohol which has been split off and of the solvent which has preferably been used, and then increases to the boiling point of the solvent used.

In the case of the particularly preferred process variant of the condensation of methyl or ethyl pivaloylacetate with 2-chloro-5-nitroaniline, a mixture of 1 mol of the aniline, 1.2 mols of the pivaloylacetic acid ester and about 2 mols of toluene as the diluent can advantageously be heated, whilst stirring, until the reaction mixture boils. The alcohol formed is then distilled off as an azeotrope with toluene, the temperature at the head of the distillation column showing the boiling point of the azeotrope for a relatively long time; using the methyl ester and the methanol/toluene azeotrope as an example, this boiling point is about 64° C. The reaction is then continued until the temperature at the head of the column shows the boiling point of toluene, namely about 110° C. After the product has been isolated, the yield which can be achieved in this way is at least 90% of the theoretical yield, relative to the nitroaniline used, and in many cases above 95% of the theoretical yield. In the case of the preferred process variant using an acetoacetic acid ester, working-up is carried out by distilling off the diluent and the excess acetoacetic acid ester. Thereafter, either the remaining distillation residue is again treated with one of the said diluents and the product is obtained as crystals, after cooling, or the product melt obtained after distillation of the diluent and the excess acetoacetic acid ester is transferred directly onto a cooling roller and obtained as a flaky product. In this last working-up variant, yields of up to 99% of the theoretical yield are possible.

The present invention also relates to another process for the preparation of 3-nitro-acetoacetanilides of the formula (I)

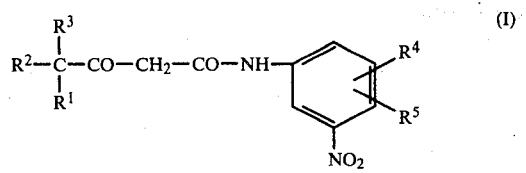

in which
R$^1$, R$^2$ and R$^3$ independently of one another represent hydrogen, alkyl, cycloalkyl or aryl, or two of the said radicals can form a cycloalkyl ring together with the C atom on which they are substituents, and
R$^4$ and R$^5$ independently of one another denote hydrogen, alkyl, aralkyl, aryl, alkoxy, alkylthio, aralkoxy, aralkylthio, aryloxy, arylthio, halogen, nitro or amino disubstituted by alkyl, aralkyl or aryl, and also
R$^4$ and R$^5$, when they are adjacent, can be parts of a fused cycloaliphatic or aromatic ring,
which is characterised in that an enamine of the formula (VIII)

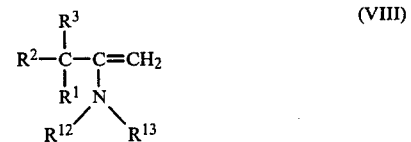

in which
R$^1$, R$^2$ and R$^3$ have the meaning indicated and
R$^{12}$ and R$^{13}$ independently of one another denote alkyl, aralkyl or aryl, or
R$^{12}$ and R$^{13}$, together with the nitrogen atom on which they are substituents, denote a nitrogen-containing heterocyclic ring which can optionally contain further hetero-atoms,
is reacted with a 3-nitro-phenyl isocyanate of the formula (IX)

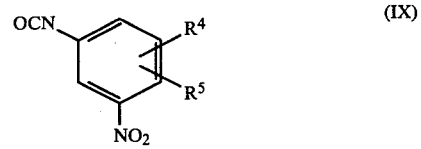

in which
R$^4$ and R$^5$ have the meaning indicated, at a temperature of −5° C. to +100° C., if appropriate in the presence of an inert diluent, in such a way that the enamine is always present in excess, and the β-amino-but-2-ene-carboxylic acid 3-nitro-anilide formed as an intermediate, of the formula (X)

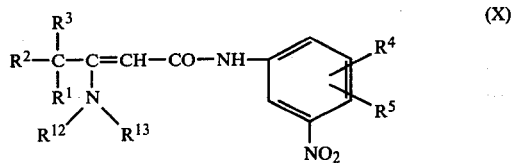

in which
R$^1$, R$^2$, R$^3$, R$^4$, R$^5$, R$^{12}$ and R$^{13}$ have the meaning indicated, is hydrolysed, if appropriate after prior isolation and purification.

For examples of the names of the individual radicals in the formulae (VIII), (IX) and (X), reference may be made to the list given above. In the case where $R^{12}$ and $R^{13}$, together with the nitrogen atom on which they are substituents, denote a nitrogen-containing heterocyclic ring, a 5- to 7-membered heterocyclic ring, such as pyrrolidine, piperidine or azepine, may be mentioned by way of example. This nitrogen-containing heterocyclic ring can contain further hetero-atoms, such as nitrogen, sulphur or oxygen. The following systems may be mentioned by way of examples: pyrazolidine, pyrazoline, imidazoline, imidazolidine, oxazoline, oxazolidine, thiazoline, thiazolidine, piperazine, morpholine or thiomorpholine.

Enamines which are suitable for the process can be prepared in a known manner from the corresponding carbonyl compounds and secondary amines, for example dimethylamine, pyrrolidine, piperidine or morpholine, and titanium tetrochloride (J. Org. Chem., 32, 213 (1967)).

Enamines of the formula (XI)

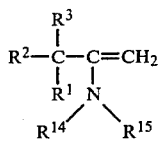

(XI)

in which $R^1$, $R^2$ and $R^3$ have the meaning indicated and $R^{14}$ and $R^{15}$ denote methyl or, together with the nitrogen atom on which they are substituents, denote the pyrrolidine, piperidine or morpholine system, are preferably used in the process according to the invention.

The use of 3,3-dimethyl-2-dimethylamino-but-1-ene of the formula (XII)

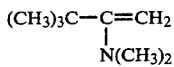

(XII)

is particularly preferred.

The 3-nitro-phenyl isocyanates of the formula (XI) can be prepared, for example, by a hitherto unpublished process, by phosgenation of the correspondingly substituted 3-nitro-anilines.

The phosgenation is effected using excess phosgene at a temperature of between $-10°$ C. and $+200°$ C., preferably in an inert solvent. 2-Chloro-5-nitro-phenyl isocyanates can be prepared by the method described in commonly owned co-pending application, Ser. No. 263,389, filed concurrently herewith entitled "2-chloro-5-nitro-phenyl isocyanate, a process for its preparation and its use", the disclosure of which is hereby incorporated herein by reference. According to that process isocyanate, such as 2-chloro-5-nitro-phenyl isocyanate, are prepared by reacting the corresponding aniline e.g. 2-chloro-5-nitro-aniline or its hydrochloride in an inert solvent at a temperature of $-10°$ to $+200°$ C. with excess phosgene. Preferably, the reaction is initiated at a temperature of $-10°$ to $+20°$ C. with excess phosgene. The reaction mixture is further treated thereafter at a temperature of $30°$ to $170°$ C. with further phosgene until the evolution of HCl ceases. A 0.1 to 10 mol excess phosgene per amino group is suitable.

3-Nitro-phenyl isocyanates of the formula (XIII)

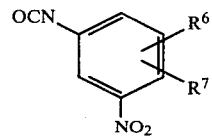

(XIII)

in which $R^6$ and $R^7$ have the meaning indicated above, are preferably used in the process according to the invention.

The use of 2-chloro-5-nitro-phenyl isocyanate is particularly preferred in the process according to the invention.

Using the reaction of 3,3-dimethyl-2-dimethyl-amino-but-1-ene with 2-chloro-5-nitro-phenyl isocyanate and hydrolysis of the resulting $\beta$-dimethylamino-$\gamma,\gamma$-dimethyl-pent-2-ene-carboxylic acid (2-chloro-5-nitro)-anilide as an example, the process according to the invention can be illustrated by means of the following equations:

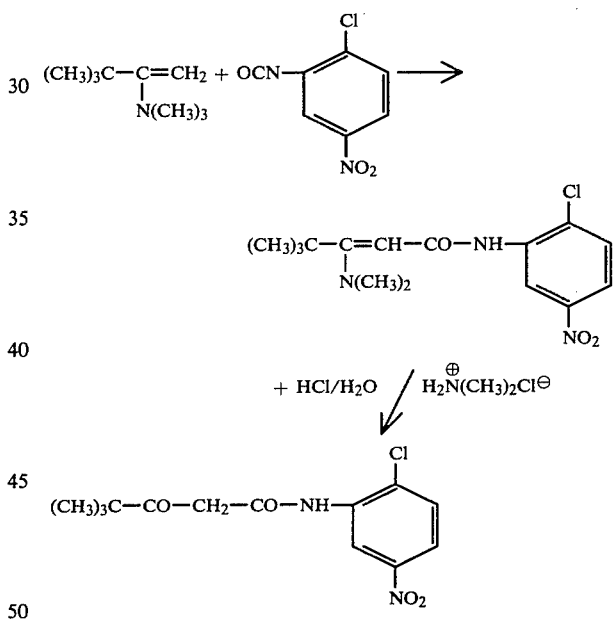

The process according to the invention is carried out at a temperature of $-5°$ C. to $+100°$ C., preferably $0°$ to $80°$ C. and particularly preferably at about room temperature.

The process according to the invention can be carried out with or without a diluent. In the case where a diluent is used, it must be inert towards the reactants. Suitable inert solvents are those which do not carry a mobile hydrogen atom, such as hydrocarbons, chlorinated hydrocarbons or ethers. Examples which may be mentioned are: benzine fractions, cyclohexane, benzene, toluene, xylene, methylene chloride, chlorobenzene, dichlorobenzene, diethyl ether, tetrahydrofuran or dioxan. Excess enamine can also be used as the diluent and can be recovered on working up the reaction mixture.

For completion, the reaction of the process according to the invention requires a molar ratio of the enamine to the phenyl isocyanate of 1:1. To avoid undesired side reactions, however, the process according to the invention is carried out in such a way that the enamine is always present in excess in the reaction mixture. An equimolar ratio of the reactants used for the reaction can only be reached again at the end of the reaction of the process according to the invention. The molar excess of the enamine over the phenyl isocyanate can be of any magnitude, in particular when using excess enamine as the solvent. A range of 1 to 5 mols of enamine per mol of phenyl isocyanate may be mentioned by way of example.

To maintain an excess of enamine in the reaction mixture, the reaction is carried out in such a way that the isocyanate, in pure or dilute form, is added in a stoichiometric or less than stoichiometric amount to the pure or dilute enamine initially introduced. The isocyanate can be added rapidly because the reaction of the process according to the invention proceeds rapidly. Of course, it is also possible initially to introduce only part of the enamine and to add the remaining enamine with the phenyl isocyanate in such a way that an excess of the enamine is present in the reaction mixture at any time during the reaction.

In the case where the process is carried out in the presence of a diluent, either the enamine initially introduced or the phenyl isocyanate added can be used, independently of one another, in pure form or in dilute form. A preferred variant of the process according to the invention uses an approximately 20 to 25% strength by weight solution of the isocyanate, as is obtained from the preparation of this isocyanate by means of hot phosgenation. By way of example, this can be a solution of the isocyanate in chlorobenzene. In this process variant, the enamine is initially introduced without another diluent.

For the subsequent hydrolysis of the intermediate initially formed, the latter is reacted with at least the equivalent amount of water. For the hydrolysis to proceed smoothly and in order to avoid troublesome side reactions, it is advantageous to maintain a pH range of 4 to 9 during this hydrolysis. This is achieved by metering an acid or a base into the reaction mixture. To avoid undesired ions in the reaction mixture, it is advantageous to use simple mineral acids, such as hydrochloric acid, sulphuric acid or phosphoric acid. The process is preferably carried out in the weakly acidic range, at pH 4 to pH 6, and particularly preferably in the region of the pH value 5. The acid to be used in this process is preferably hydrochloric acid.

The hydrolysis of the intermediate, using hydrochloric acid, can be carried out by adding the required amount of water and then adding concentrated aqueous hydrochloric acid dropwise, the rate of the dropwise addition being adjusted so that a pH value of about 5 is maintained. The isolation of the desired product, after phase separation and, if appropriate, after filtration, can be carried out in accordance with customary methods, for example by cooling and/or concentrating the organic phase and crystallising the reaction product. Another advantageous variant of the hydrolysis is characterised in that gaseous hydrogen chloride is passed into the reaction mixture and the intermediate initially formed in the process according to the invention is thus precipitated as the immonium salt. After the total or partial removal of the organic solvent, the precipitated immonium salt can be hydrolysed to the desired end product by stirring with water, if appropriate with the addition of basic substances, such as aqueous sodium hydroxide solution, at a pH value of about 5. It can be advantageous to use this variant of the hydrolysis if the process is carried out in the presence of one of the said diluents.

The possibility of isolating the resulting intermediate in pure form or in the form of the immonium salt makes it possible to carry out an intermediate purification, for example by recrystallisation, and thereby to achieve a particularly high purity of the end product. However, in the case where the purity of the end product without intermediate isolation and purification of the intermediate is sufficient for the subsequent use, it is also possible to dispense with this intermediate isolation.

The invention therefore also comprises the intermediates formed during the condensation of enamines of the formula (VIII) with 3-nitro-phenyl isocyanates of the formula (IX), the said intermediates being in the free form of the formula (X) or in the form of their immonium salts with hydrochloric acid, of the formula (XIV)

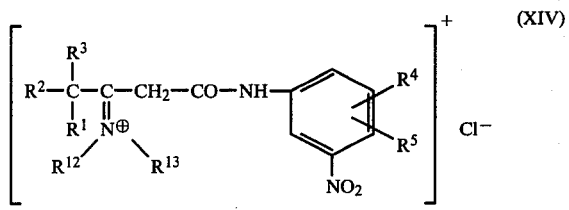

in which
R$^1$, R$^2$, R$^3$, R$^4$, R$^5$, R$^{12}$ and R$^{13}$ have the meaning indicated.

The 3-nitro-acetoacetanilides which can be prepared, in the process according to the invention, from an enamine and 3-nitro-phenyl isocyanate can be obtained in a yield of about 90 to 95% of the theoretical yield of isolated products.

The 3-nitro-acetoacetanilides of the formula (I), according to the invention, can be used for the synthesis of coupling components for colour photography. Thus, for example, 2-chloro-5-nitro-pivaloyl-acetanilide can be converted, by reduction with catalytically activated hydrogen, to 2-chloro-5-amino-pivaloyl-acetanilide, and this can be reacted further with 2,4-di-tert.-amylphenoxybutyryl chloride to give pivaloylacetic acid 2-chloro-5-(2,4-di-tert.-amyl-phenoxybutyramido)-anilide. This last compound is known as a coupling component for colour photography (U.S. Pat. No. 3,265,506, U.S. Pat. No. 3,384,657 and German Auslegeschrift No. 1,124,356).

Specifically, 3-nitro-acetoacetanilides, including in particular, 2-chloro-5-nitro-pivaloyl-acid anilide can be converted to coupling components by the process described in commonly owned co-pending application, Ser. No. 263,386, filed concurrently herewith entitled "Process for the preparation of pivaloylacetic acid 2-chloro-5-[4-(2,4-di-tert.-amyl)-phenoxybutyramido]-anilide", the disclosure of which is specifically incorporated herein by reference. According to the procedure therein disclosed, a pivaloylacetic acid anilide, such as pivaloylacetic 2-chloro-5-nitro-anilide, is reduced by contact with hydrogen in the presence of an organic compound of an element of main group V of the periodic system (Mendeleev) in an inert solvent at a temperature of 0° to 150° C. The corresponding amino compound obtainable by this reaction is then reacted further with a 4-(2,4-di-tert.-amyl)-phenoxybutyryl halide at a temperature of −50° to +50° C. in an organic solvent, if appropriate in the presence of a base. The hydrogenation can conveniently be carried out at 20° to 80° C., using an amine of an element of group V of the periodic system e.g. pyridine.

EXAMPLE 1

137 g of methyl pivaloylacetate and 130 g of toluene, together with 124.5 g of 2-chloro-5-nitro-aniline, are initially introduced into a 1 liter stirred apparatus with a 30 cm long, metal-coated Vigreux column with a column head, and are heated to the boil, whilst stirring. The bottom temperature increases from 120° C. to 145° C. in the course of 10 hours. The transition temperature increases from 64° C. to about 110° C.

About 112 ml of toluene/methanol mixture are taken off during the distillation time, this being equivalent to about 10 to 12 ml of distillate/hour.

The residue in the flask is cooled with iced water, whilst stirring, and the thick crystal mass formed is filtered off and washed with 3 times 30 ml of cold toluene. After drying in vacuo at 50° C., 190 g (90.9% of the theoretical yield, based on nitroaniline) of pivaloyl-2-chloro-5-nitroanilide remain. Yellow crystals, melting point 118° to 119° C.

|  | Elementary analysis: | | | | |
| --- | --- | --- | --- | --- | --- |
|  | C | H | N | Cl | O |
| calculated | 52.3% | 5.0% | 9.4% | 11.9% | 21.5% |
| found | 52.5 | 4.8 | 9.6 | 11.8 | 21.3 |
|  | 52.4 | 4.7 | 9.6 | 11.7 | 21.6 |

EXAMPLE 2

34.5 g of a 23.0% strength solution of crude 2-chloro-5-nitrophenyl isocyanate in chlorobenzene (about 25 ml; 0.04 mol) are added dropwise at room temperature, in the course of 20 minutes, whilst stirring, to 5.5 g of 3,3-dimethyl-2-dimethylamino-but-1-ene (93% pure; 0.04 mol). The mixture is subsequently stirred for 5 minutes. 10 ml of water are then added and about 3.9 ml of concentrated HCl are added dropwise, whilst stirring vigorously, in such a way that the pH value does not fall below 5 and is finally kept at this value. This requires about 1.5 to 2 hours. The mixture is subsequently stirred for a further ½ hour. The precipitated product is filtered off and the organic phase is concentrated to about 10 ml and cooled to −15° C., further products precipitating out. After drying in vacuo at 50° C., 10.6 g (91% of theoretical yield) of pivaloyl-2-chloro-5-nitroacetanilide, with a melting point of 116° to 119° C., remain.

EXAMPLE 3

180 g (1.0 mol) of 2-chloro-5-nitroaniline (96% pure) in solid form are introduced at 0° C., in the course of about 30 minutes, whilst stirring thoroughly, into a solution of 145 ml (207 g, 2.1 mols) of phosgene in 800 ml of chlorobenzene. The yellow-brown suspension is heated to 55° C. A slow stream of phosgene is passed in during this time, so that excess phosgene boils under reflux. The suspension clears to give a solution in the course of 4 hours, HCl being generated. The solution is subsequently phosgenated for a further hour.

Excess phosgene and chlorobenzene are distilled off until the residual volume is 600 ml. An approximately 23% strength by weight solution of 2-chloro-5-nitrophenyl isocyanate in chlorobenzene is formed, which has a phosgene content of less than 0.05%.

Content after titration: 188.3 g of isocyanate=95% of theory.

On distillation over a column which can be heated, 183 g of 2-chloro-5-nitro-phenyl isocyanate (99% pure) are obtained at a head temperature of about 130° C. and a pressure of 1 mbar. This corresponds to 93% of the theoretical yield. The melting point of the product is 93°–95° C.

EXAMPLE 4

480 g of the solution of crude 2-chloro-5-nitrophenyl isocyanate according to Example 3 (21.1% strength, 0.56 mol, 350 ml) are added dropwise at room temperature, in the course of about 30 minutes, to a stirred solution of 75.8 g of 3,3-dimethyl-2-dimethylamino-but-1-ene (94% pure, 0.56 mol) in 300 g (270 ml) of dry chlorobenzene. The mixture is subsequently stirred for 10 minutes, the dropping funnel is replaced by a gas inlet tube and dry hydrogen chloride is passed in at room temperature. A temperature of about 20° C. is maintained by cooling. After 2–3 minutes, the immonium chloride of β-dimethylamino-γ,γ-dimethyl-pent-2-ene-carboxylic acid (2-chloro-5-nitro)-anilide starts to precipitate out. The mass formed becomes increasingly viscous but can be stirred thoroughly. When no more HCl is taken up, the precipitate is filtered off on a glass frit and washed with twice 100 ml of dry chlorobenzene. The filter cake on the frit is now treated with 150 ml of water and stirred. After 3–5 minutes, the immonium salt goes into solution. During this time, the temperature increases to 35° C. Two clear phases are formed, namely an aqueous lower phase containing immonium salts and an upper phase consisting of chlorobenzene which had been retained. Concentrated sodium hydroxide solution is now added dropwise, whilst stirring vigorously, until a pH value of about 5 is reached (about 40 ml). The temperature increases to about 65° C. during this addition and the pivaloyl-2-chloro-5-nitro-acetanilide starts to crystallise from the chlorobenzene phase. A phase change takes place during the neutralisation. The organic phase which now contains the product sinks to the bottom and the aqueous phase containing dimethylammonium chloride settles at the top. The mixture is subsequently stirred for a further 3 hours and finally cooled to 0° C. The product is now filtered off and washed with twice 100 ml of water. The chlorobenzene phase can be recycled into the hydrolysis of the next batch, either directly or after precipitating remaining pivaloyl-2-chloro-5-nitro-acetanilide by cooling to −15° C., because it does not contain any other impurities apart from the pivaloyl-2-chloro-5-nitro-acetanilide. In this way, 150–160 g of pivaloyl-2-chloro-5-nitro-acetanilide, with a melting point of 118°–120° C., were obtained after drying. This corresponds to 90–95% of the theoretical yield.

What is claimed is:

1. 2-Chloro-5-nitro-pivaloyl-acetanilide.

* * * * *